United States Patent [19]

Bock

[11] Patent Number: 5,546,624

[45] Date of Patent: * Aug. 20, 1996

[54] APPARATUS TO SELECTIVELY COUPLE ULTRANSONIC ENERGY IN A THERAPEUTIC ULTRANSONIC TOOTHBRUSH

[75] Inventor: Robert T. Bock, Brewster, N.Y.

[73] Assignee: Sonex International Corporation, Brewster, N.Y.

[ * ] Notice: The term of this patent shall not extend beyond the expiration date of Pat. No. 5,369,831.

[21] Appl. No.: 325,127

[22] Filed: Oct. 18, 1994

Related U.S. Application Data

[63] Continuation-in-part of Ser. No. 911,489, Jul. 10, 1992, Pat. No. 5,247,716, and a continuation-in-part of Ser. No. 674,123, Mar. 25, 1991, Pat. No. 5,138,733, and a continuation-in-part of Ser. No. 84,979, Jun. 25, 1993, Pat. No. 5,369,831.

[51] Int. Cl.[6] .................................................. A61C 17/20
[52] U.S. Cl. ........................ 15/22.1; 15/167.1; 433/119
[58] Field of Search .................................. 15/22.1, 22.2, 15/22.4, 167.1; 433/119, 216

[56] References Cited

U.S. PATENT DOCUMENTS

| | | | |
|---|---|---|---|
| 3,335,443 | 8/1967 | Parisi et al. | 15/22.1 |
| 3,375,820 | 4/1968 | Kuris et al. | 15/22.1 |
| 3,760,799 | 9/1973 | Crowson | 433/119 |
| 3,980,906 | 9/1976 | Kuris et al. | 15/22.1 |
| 4,192,035 | 3/1980 | Kuris | 15/22.1 |
| 4,333,197 | 6/1982 | Kuris | 15/22.1 |
| 4,787,847 | 11/1988 | Martin et al. | 433/119 |

*Primary Examiner*—David Scherbel
*Assistant Examiner*—Tony G. Soohoo
*Attorney, Agent, or Firm*—Watson Cole Stevens & Davis, P.L.L.C.

[57] ABSTRACT

An improved therapeutic ultrasonic toothbrush for daily removal of soft plaque, disruption of the bacterial colonization process within the gingival pockets, the reduction of the recurrence of aphthous stomatitis, and for the acceleration of the healing of the sores of the oral cavity. The device includes a handle constructed of a rigid material, a battery pack, an electronics driving module, a piezoelectric member, and a removable brush head. The piezoelectric crystal resonates, expands and contracts volumetrically, in tune with the frequency supplied by the electronics driving module and thereby converts the electronic energy into sound-wave energy. The sound waves loosen up the bound between the bacterial plaque and the teeth and disrupt the bacterial colonization process within the periodontal pockets and the mucous membranes of the oral cavity. Ultrasonic emission from the back side of the brush accelerates healing of sores of the oral cavity. A variation of the device provides directional control of the ultrasonic output to maximize either the dental or the dermatological benefits of the brush.

30 Claims, 12 Drawing Sheets

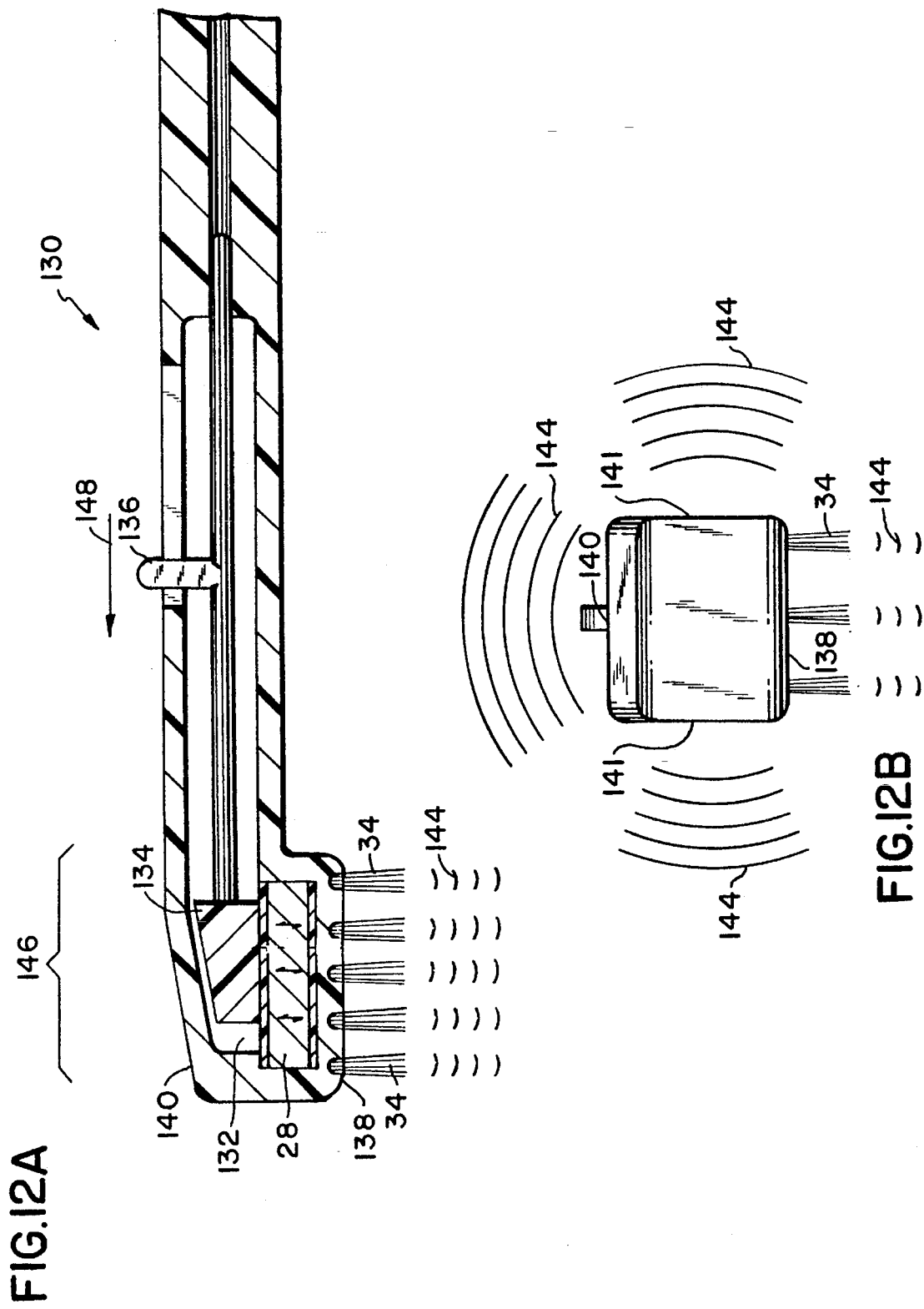

ically, the invention is concerned with an apparatus facilitating the use of ultrasonic energy to assist an otherwise manual toothbrush in loosening and removing soft plaque from the teeth of the user on a substantially daily basis. A specific concern of the invention is an apparatus that carries the bristle clusters, which is readily replaceable as wear of the bristles occur. Another concern is the therapeutic treatment of oral tissue, and specifically treatment and prevention of mouth sores. Yet another concern is to provide particular configurations to remove plaque, to treat gingivitis, and to prevent or treat aphthous stomatitis commonly known as canker sores.

5,546,624

APPARATUS TO SELECTIVELY COUPLE ULTRASONIC ENERGY IN A THERAPEUTIC ULTRASONIC TOOTHBRUSH

RELATED APPLICATION

This application is a continuation-in-part of U.S. patent application Ser. No. 07/911,489, filed Jul. 10, 1992 now U.S. Pat. No. 5,247,716, entitled "Removable Brush-Head for Ultrasonic Toothbrush"; U.S. Pat. No. 5,138,733, which issued Aug. 18, 1992, a c-i-p of U.S. patent application Ser. No. 07/674,123, filed Mar. 25, 1991 entitled "Ultrasonic Toothbrush"; and a c-i-p of U.S. patent application Ser. No. 08/084,979, filed Jun. 25, 1993, now U.S. Pat. No. 5,369,831 entitled "Therapeutic Ultrasonic Toothbrush".

BACKGROUND OF THE INVENTION

This invention relates to toothbrushes. More particularly, the invention is concerned with an apparatus facilitating the use of ultrasonic energy to assist an otherwise manual toothbrush in loosening and removing soft plaque from the teeth of the user on a substantially daily basis. A specific concern of the invention is an apparatus that carries the bristle clusters, which is readily replaceable as wear of the bristles occur. Another concern is the therapeutic treatment of oral tissue, and specifically treatment and prevention of mouth sores. Yet another concern is to provide particular configurations to remove plaque, to treat gingivitis, and to prevent or treat aphthous stomatitis commonly known as canker sores.

Numerous attempts have been made to develop an apparatus to remove plaque or tartar from the surface of the teeth. Some of the devices utilized sonic and/or ultrasonic energy. The devices utilizing sonic or ultrasonic energy can be grouped into three distinct categories.

One approach is the utilization of only fluids as a medium of energy transmission and plaque removal by placing an ultrasonic transducer into the middle of the mouth. This approach is impractical and physiologically dangerous due to the high energy levels it requires to be effective in absence of any mechanical scrubbing, and the uncontrolled, variable, user dependent distance between the transducer and the teeth. A typical example is U.S. Pat. No. 3,760,799.

The second approach is the application of ultrasonic energy to vibrate the toothbrush. While these teachings are aged, no application to date has demonstrated the practical feasibility of carrying out the science in this manner. The significant drawback of some of these proposals is that the toothbrush or applicator is solidly attached, otherwise fixed to the transducer, making replacement of the brush difficult and expensive, taking the device out of the economically affordable daily dental hygiene device category for the general population. Examples of these devices can be found in the following U.S. Pat. Nos.: 4,192,035, 4,333,197 and 4,787,847.

The third and only theory reduced to practice to date is to remove hardened or calcified plaque colonies from the surface of the teeth on infrequent periodical basis. This art has been made available to professional dentists in the form of a high energy device that couples the ultrasonic energy to the teeth by a metal probe. While safe in the hands of the highly skilled and professionally trained dentists or hygienists, these devices are not suitable for daily use by the general population. Such devices could case damage to the surface of the teeth and the surrounding tissue when utilized by untrained novice consumers. What has occurred to date is that notwithstanding the teachings of the prior art, the ability to utilize ultrasonic energy to assist the consumer in the daily maintenance of oral hygiene in a safe and effective manner has remained unsolved.

In addition, the treatment of mouth sores in the oral cavity generally requires separate therapy which is time consuming and inconvenient. A combined cleaning and tissue therapy general purpose instrument is disclosed in U.S. Patent application Ser. No. 08/084,979. In some instances optimum treatments for the different therapeutic needs of different individuals may require a more specialized instrument.

OBJECTS AND ADVANTAGES OF THE INVENTION

Responding to the above-described unsolved needs, this invention provides an ultrasonic toothbrush that is safe and effective to assist the consumer in the daily maintenance of oral hygiene. The invention attains this goal by positioning a piezoelectric transducer in the head section of an otherwise manual toothbrush. The piezoelectric crystal, resonating at or about its resonant frequency, emits ultrasonic waves between the bristles and couples the energy to the surface of the teeth via the dentifrice in the users mouth.

An object of the present invention is to provide a safe ultrasonic energy coupling mechanism to the user's teeth to dislodge and remove soft plaque.

Another object of the invention is to provide an effective cleaning device while reducing the ultrasonic energy level to the point where the daily application in the hands of an untrained novice will not harm the surface of the teeth or the surrounding soft tissue.

A further object is to provide an inexpensive removable brush component, independent from the sealed ultrasonic energy emitter, that can be easily replaced by the consumer. The brush component must provide for adequate interface between the surfaces of the main body containing the piezoelectric transducer, and the surfaces of the brush component, for efficient transmission of the ultrasonic energy.

Yet another object of the invention is to provide means for the daily cleaning of teeth which also allows for the treatment and prevention of mouth sores at the same time.

A further object of the invention is to provide a switchable configuration where the majority of the ultrasonic energy can be directed toward the bristles for treatment of gingivitis or directed toward the back of the brush for the treatment of aphthous stomatitis for the person who is prone to attacks of canker sores and gingivitis at different times.

Yet another object of the invention is to provide optimized configurations for people who have a problem with either gingivitis or aphthous stomatitis, but not necessarily both.

A further object of the invention is to provide a low cost universal configuration with improved circumferential ultrasonic transmission capability.

BRIEF DESCRIPTION OF THE DRAWINGS

In the accompanying drawings, in which certain modes of carrying out the present invention are shown for illustrative purposes:

FIG. 12A is similar to FIG. 12 except that the switchable device is shown in an intermediate position;

FIG. 12B is an end view of FIG. 12A;

DESCRIPTION OF THE INVENTION

Figure 1:
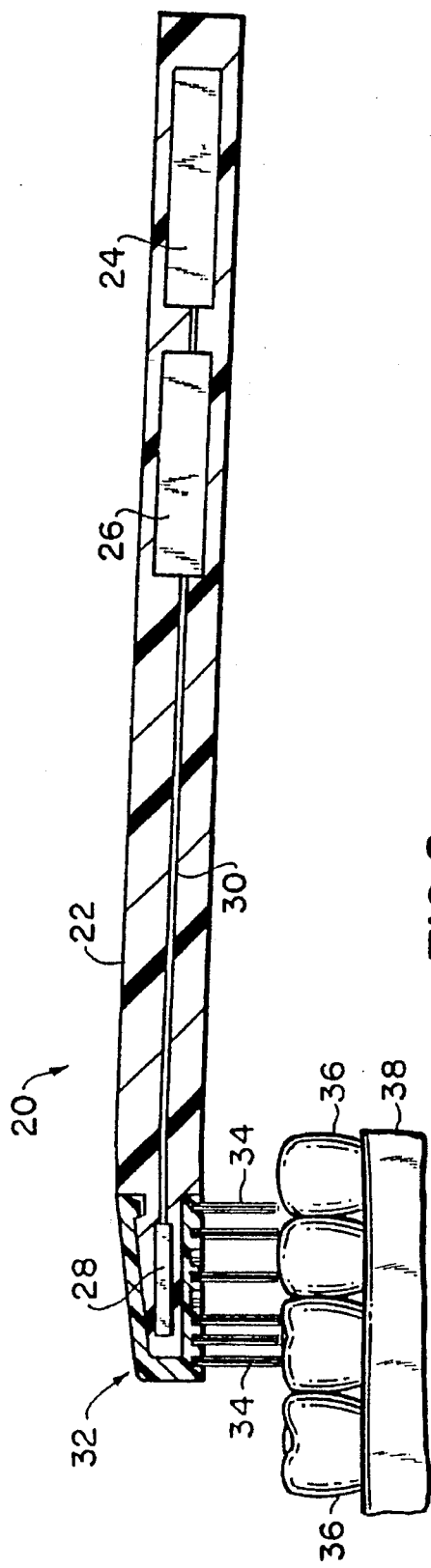
FIG. 1 shows a longitudinal cross section of the invention in the replaceable brush-head configuration, including a battery powered driving circuitry.

Referring in detail to the drawings, the reference numerals herein refer to the like numbered parts in the drawings. In the following discussion, unless otherwise qualified, for convenience the term "ultrasonic" refers to either subsonic, sonic, or ultrasonic frequencies. As hereinafter described with respect to an embodiment of the invention, combinations of such frequencies may be employed.

An ultrasonic toothbrush 20, in accordance with the present invention, is shown in FIG. 1. The toothbrush comprises of a handle 22 constructed of a rigid material, a battery pack 24, an electronics driving module 26, a piezoelectric transducer 28, connecting wiring 30, and a removable brush-head 32 made of a flexible material that encompasses a plurality of bristle clusters 34. The toothbrush is shown in a typical cleaning position, the bristle clusters 34 in contact with the teeth 36 in the oral cavity 38. The low voltage DC energy supplied by the battery pack 24 is converted to an ultrasonic frequency DC current by the electronics driving module 26, which is connected to the piezoelectric transducer 28 by the connecting wiring 30. The piezoelectric crystal resonates, expands and contracts volumetrically, in tune with the frequency supplied by the electronics driving module 26 and thereby converts the electronic energy into sound-wave energy. The sound-waves driving the dentifrices or other sonic medium in the mouth of the user against the teeth 36 causing mild cavitation within the dentifrices at the junction with the teeth, resulting in a loosening effect on the soft plaque on the surface of the teeth and in the periodontal pockets formed in the gums around the neck of the teeth. The loosened soft plaque is then dislodged by the bristle clusters 34 of the toothbrush 20 by the normal brushing movements of the user. The ultrasonic energy also beneficially affects adjacent lip, gum and facial tissue inside the oral cavity as hereafter noted.

The length of the bristle clusters 34 is selected to space the transducer 28 within an effective and controlled optimum distance to the teeth, allowing the reduction of the sound energy to biologically safe levels for routine daily application without causing harm to the surface or root structure of the teeth, and the surrounding soft tissue.

Figure 3:
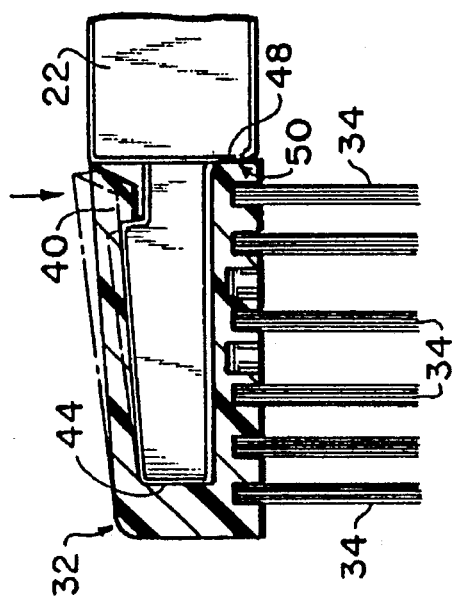
FIGS. 2 and 3 show the lock-in attachment methodology of the brush-head to the handle of the ultrasonic device, in a cross sectional view.
Figure 2:
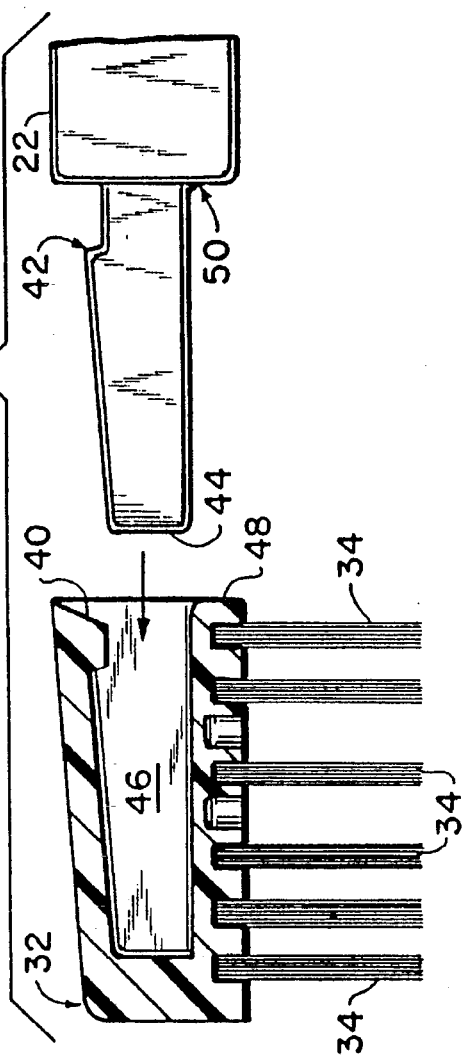

FIGS. 2 and 3 illustrate the lock-in attachment methodology of the brush-head 32 to the handle 22. The achieve a firm attachment, the brush-head 32 incorporates a tapered tongue section 40 and the handle incorporates a matching groove 42. To install a replacement brush-head 32, the user engages the rigid nose 44 section of the handle 22 with the flexible mouth 46 section of the brush-head 32. Upon engagement, the user forces the brush-head 32 upon the handle 22 until the movement is stopped by the lower mating surfaces 48 and 50 of the brush-head 32 and handle 22 respectively, and the tongue 40 snaps into the groove 42.

Figure 4:
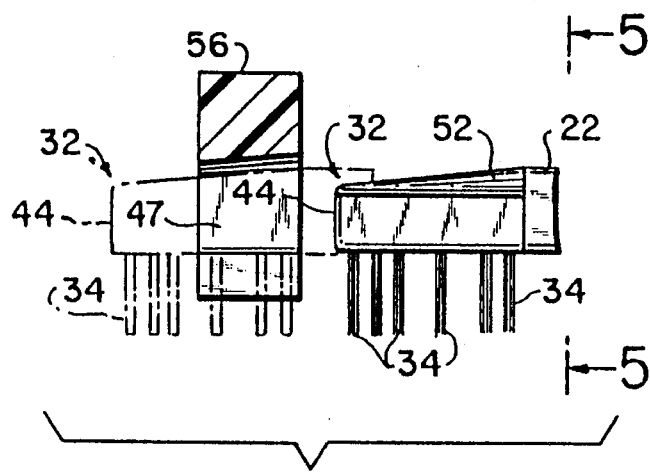
FIGS. 4, 5 and 6 show the brush-head unlocking tool and the removal methodology of the brush-head from the main body of the device.
Figure 5:
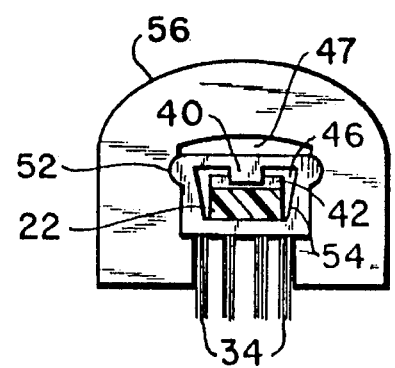
Figure 6:
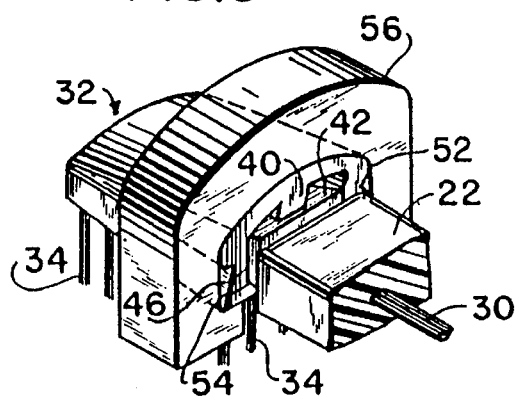

FIGS. 4, 5 and 6 illustrate the un-locking methodology of another configuration brush-head 32 from the handle 22. The brush-head 32 incorporates a tapered abutment 52 on each side that increases in size towards its mouth 46. The internal cavity of the mouth 46 is tapered 54, and increasing in size toward the abutments 52, forming a gap between the brush-head 32 and the handle 22 adjacent to the abutments 52. A removal tool 56 constructed of a material with superior strength and rigidity to the flexible brush-head 32 material, comprises a cavity that matches the lower and straight side dimensions of the brush-head 32 but larger than the brush-head 32 in the vertical dimension. As the user slides the rigid removal tool 56 upon the flexible brush-head 32, the sides with the abutments 52 of the brush-head 32 deform inwardly, causing the top section of the brush-head 32 with the tongue 40 to flex into the gap 47, out of the groove 42 of the handle 22, thereby unlocking the brush-head 32 from the handle 22.

FIGS. 6A–6E show an embodiment of the attachment and removal methodology of the brush-head to and from the handle of the device.

Figure 6A:
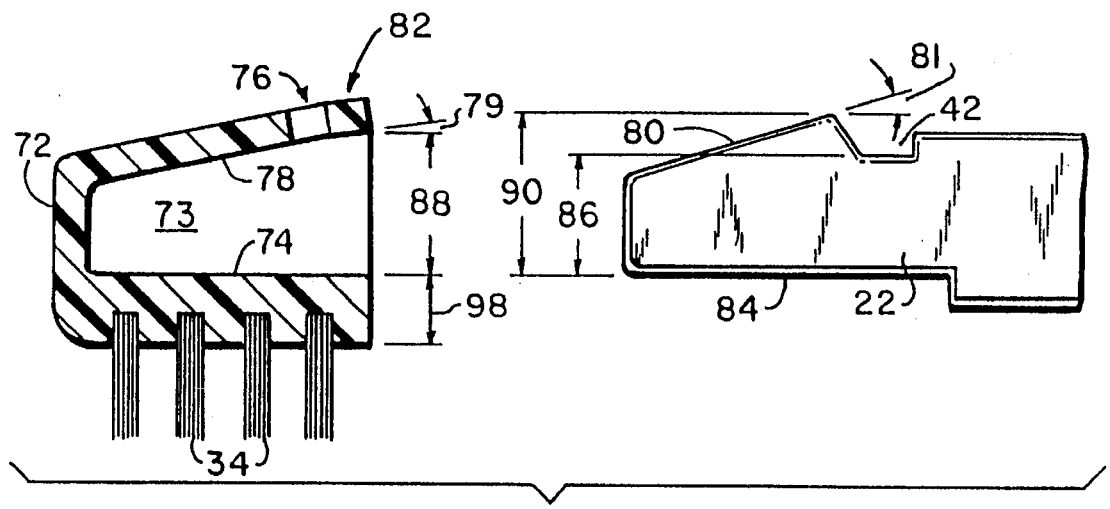
FIGS. 6A–6E show an embodiment of the attachment and removal methodology of the brush-head to and from the handle of the device.

FIG. 6A shows the preferred brush-head 72 constructed of a flexible material with varying wall thicknesses, incorporating a cavity 73 having a flat bottom surface 74 adjacent to the bristle clusters 34 and a tapered upper surface 78 opposite to the bristle clusters 34. The wall opposite to the bristle clusters 34 incorporates a slot 76 for the purpose of locking the brush-head 72 into place on the handle 22 and to secure it against accidental removal. The handle 22 constructed of a rigid material, incorporates a flat bottom surface 84 and a tapered upper surface 80, wherein the angle 81 of the tapered upper surface 80 is larger than the angle 79 of the tapered upper inside surface 78 of the brush-head 72 cavity 73. The handle 22 also comprises a groove 42 adapted to receive the flexible end portion 82 of the brush-head 72. The dimension 86 of the handle 22 is approximately the same as the dimension 88 of the brush-head 72, while the dimension 90 of the handle 22 is significantly larger than the dimension 88 of the brush-head 72.

Figure 6B:
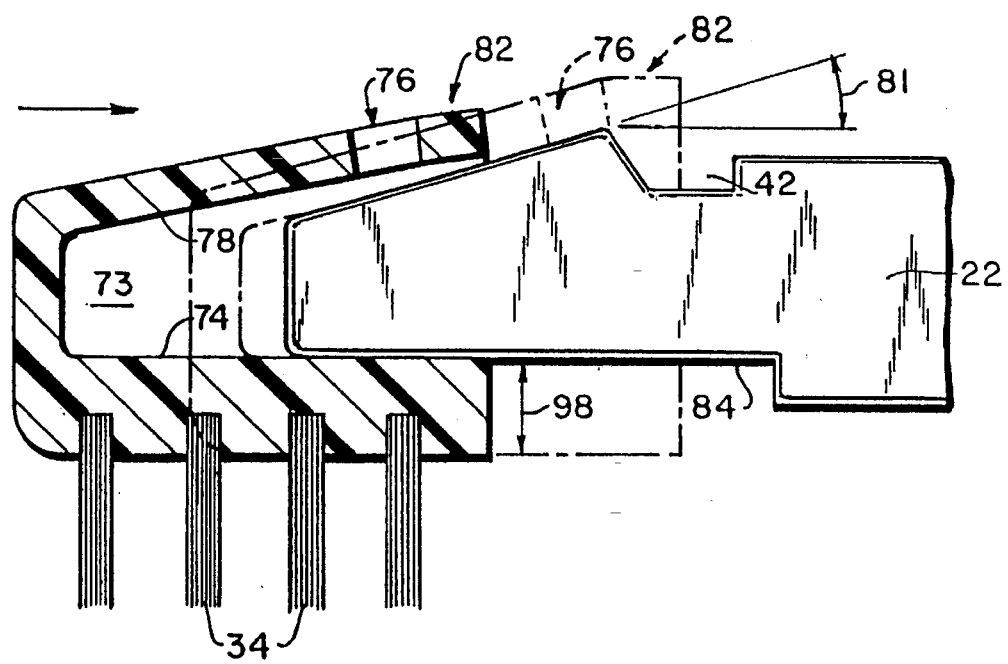

FIG. 6B shows the installation process of the brush-head 72 onto the handle 22. The user aligns the flat inside surface 74 of the brush-head 72 with the flat outer surface 84 of the handle 22, then proceeds to push the brush-head 72 onto the handle 22.

Figure 6C:
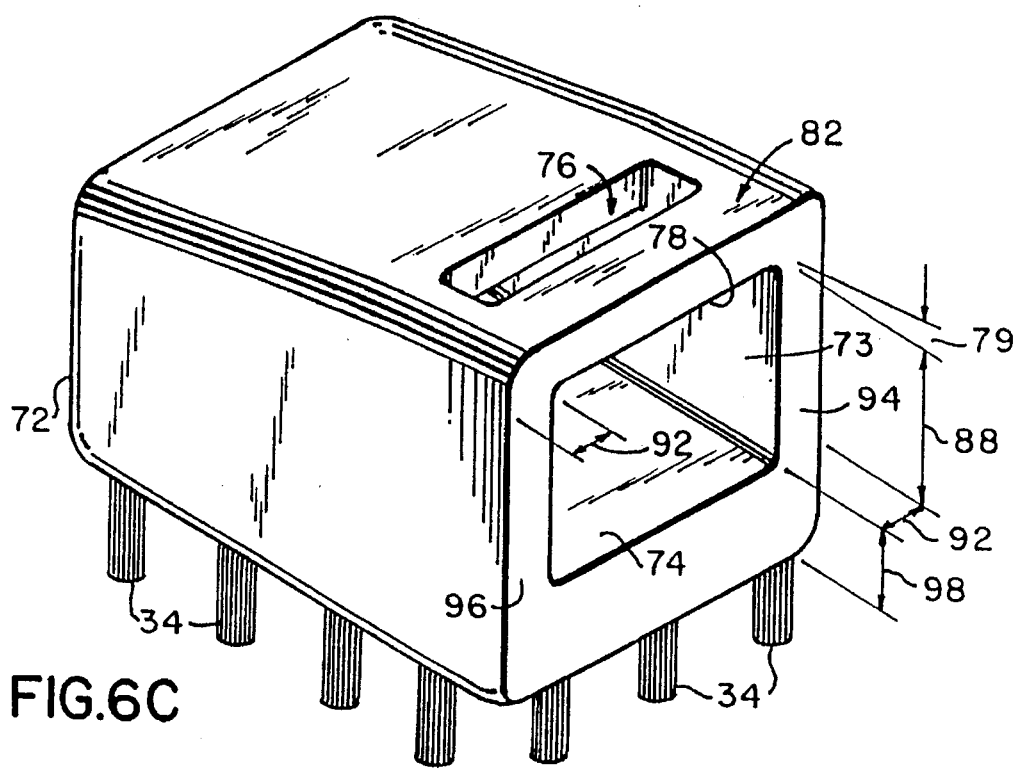
Figure 6C:
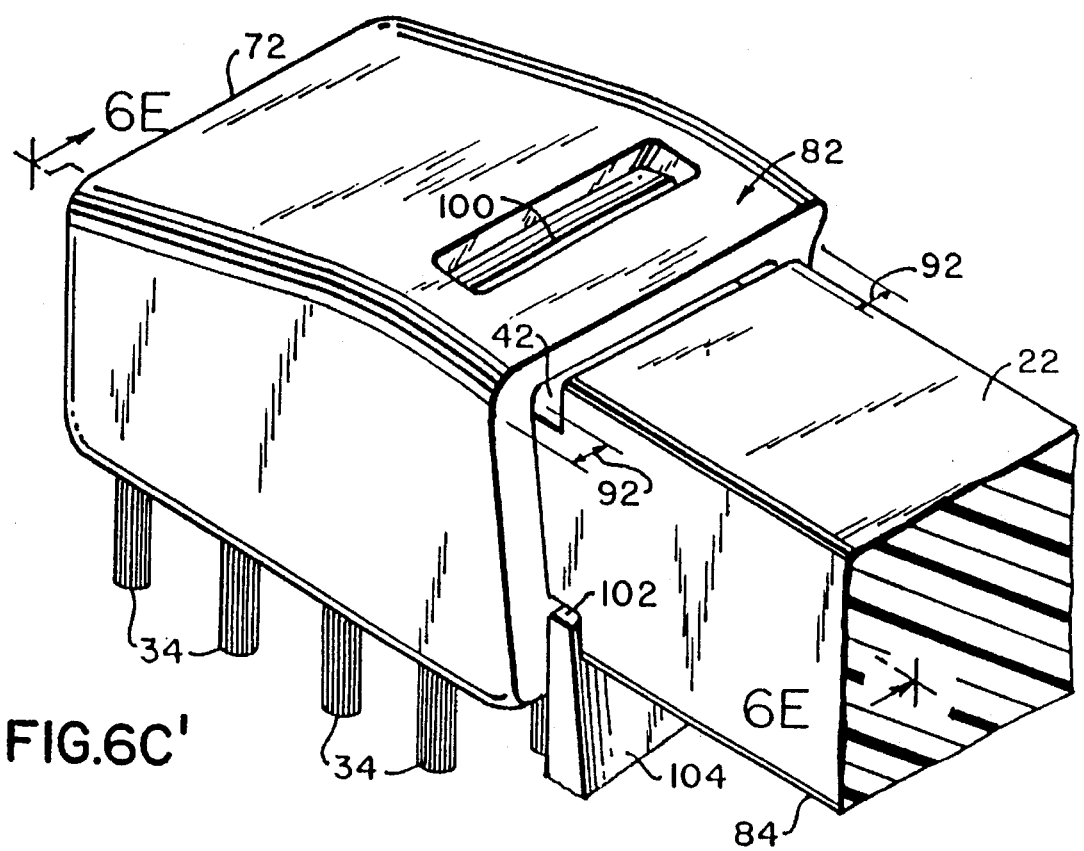

During the installation process, as shown in FIG. 6C and 6C', the larger angle 81 of the handle 22 expands the walls 94 and 96 of the brush-head 72 which is constructed with a smaller angle 79. The vertical wall thickness 92 of the brush-head 72 is designed to be substantially thinner than the bottom section 98 to assure that the expansion and the accompanying deformation of the brush-head 72 takes place within the side walls 94 and 96. The thickness of the bottom section 98 is calculated to assure that the inside flat surface 74 adjacent to the bristle clusters 34 of the brush-head 72 remains flat and not deformed by the expansion forces, and remains in intimate contact with the surface 84 of the handle 22.

Figure 6D:
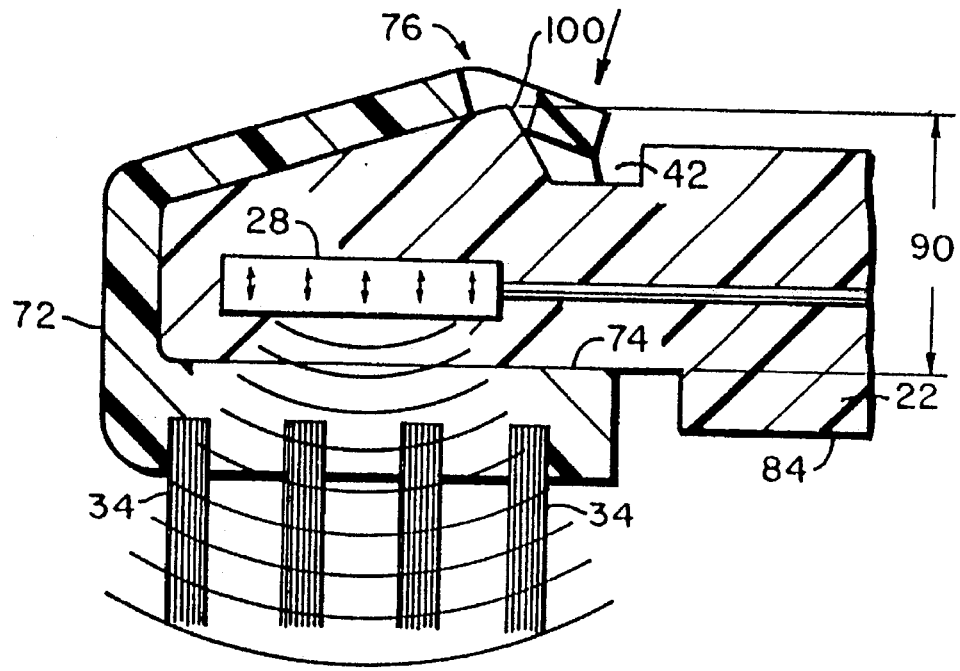

FIG. 6D describes the ultrasonic energy transmission methodology from the piezoelectric transducer 28 through the brush-head 72. When the brush-head 72 is pushed fully onto the handle 22, and the side walls 94 and 96 are expanded, the entire inside surface 74 of the brush-head 72 is forced into a tight and intimate contact with the outside surface 84 of the handle 22 by the tensional forces generated in the side walls 94 and 96 of the brush-head 72. This feature of matching surfaces in intimate contact is important for the efficient transmission of the ultrasonic energy from the piezoelectric crystal 28 through the handle 22 or the brush-head 72 and the bristle clusters 34. The volumetric expansion and contraction of the piezoelectric transducer 28 indicated by the double headed arrows generates the sound waves indicated by the curved lines, that are transmitted to the handle 22 and in turn to the brush-head 72 external surfaces and to the bristle clusters 34. The thickness 92 of the side walls 94 and 96 are also calculated to assure that the stress generated by the expansion force does not exceed the yield strength of the side walls 94 and 96. When designed in this manner, the stress generated in the side walls 94 and 96 will provide a force to maintain intimate contact between the surface 74 of the brush-head 72 and the surface 84 of the handle 22 throughout the life cycle of the brush-head 72.

Figure 6E:
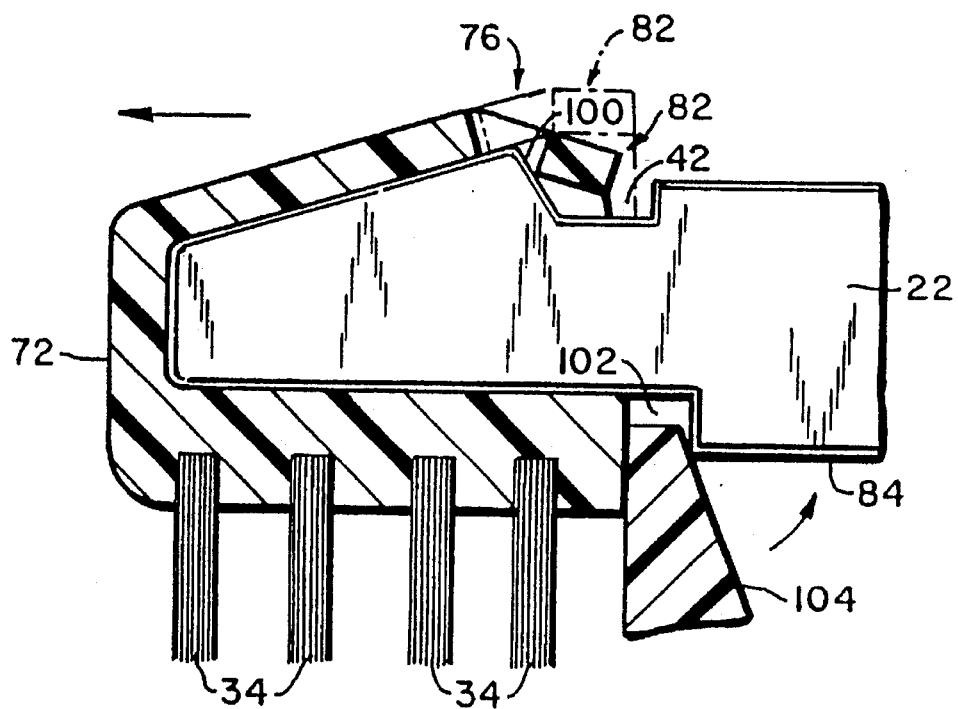

FIG. 6E shows the locking methodology of the brush-head 72 to the handle 22. As the end portion 82 of the brush-head 72 next to the slot 76 passes over the thickest dimension 90 of the handle 22, it is positioned directly above the groove 42 of the handle 22. The tensional forces in the side walls 94 and 96 pull the flexible end portion 82 of the brush-head 72 into the groove 42 of the handle 22, thereby locking the brush-head 72 into position on the handle 22. The angularity of the surface 100 is designed to prevent movement of the brush-head 72 by the forces generated of the bristle clusters 34 as they are rubbed against the teeth of the user, but to allow the removal of the brush-head 72 from the handle 22 when a significant axial pulling force is applied by the user.

FIG. 6E further shows the removal methodology of the brush-head 72 from the handle 22. The user presses a wedge 104 into a gap 102 formed between the brush-head 72 and the handle 22, perpendicular to the longitudinal axis of the handle 22. As the wedge penetrates, it widens the gap 102 and forces the brush-head 72 away from the handle in an axial motion, while the flexible end portion 82 of the brush-head 72 rides up on the angle 100 of the handle 22, releasing the brush-head 72. In practice, numerous other tools could replace the wedge 104 in the action of widening the gap. A screwdriver or a coin being twisted in the gap could fulfill the same function.

Figure 7:
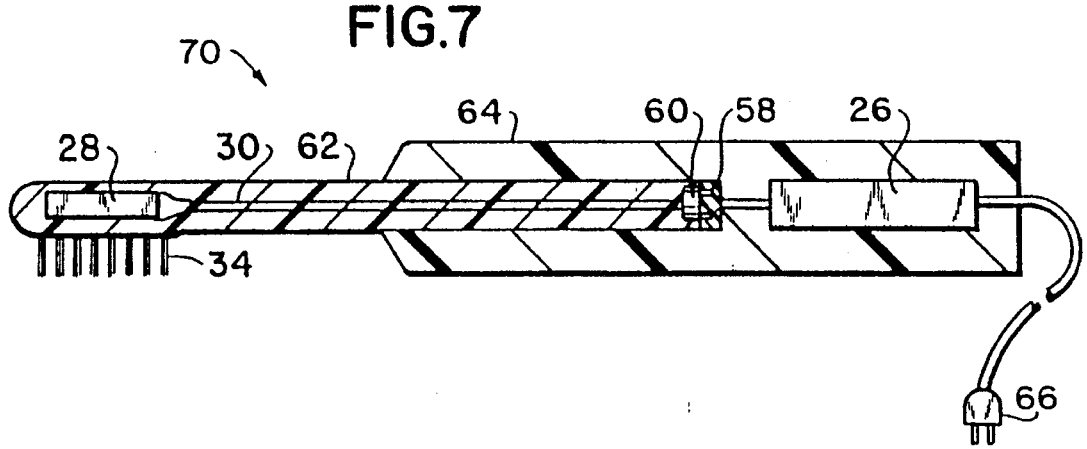
FIG. 7 shows an alternative embodiment of the invention where the removable bristle support includes the piezoelectric crystal.

FIG. 7 shows an alternative embodiment of the invention, where the ultrasonic toothbrush 70 comprises of a AC line connector 66, a handle 64, an electronics module 26, a low voltage high frequency DC connector 58, and a replaceable brush element 62 that is further comprised of a plurality of bristle clusters 34, a piezoelectric transducer 28, connecting wiring 30, and another connector 60. The electronics module is energized by conventional AC house current through the line connector 66. The AC house current is converted to a low voltage, ultrasonic frequency DC current by the electronics module 26, which is connected to the piezoelectric transducer 28 by the connecting wiring 30 through the connectors 58 and 60. The piezoelectric crystal resonates, expands and contracts volumetrically, in tune with the frequency supplied by the electronics driving module 26 and thereby converts the electronic energy into sound-wave energy. The sound-waves driving the dentifrices in the mouth of the user against the teeth 36 causing mild cavitation within the dentifrices at the junction with the teeth, resulting in a loosening effect on the soft plaque on the surface of the teeth and in the periodontal pockets formed in the gums around the neck of the teeth. The loosened soft plaque is then dislodged by the bristle clusters 34 of the toothbrush 70 by the normal brushing movements of the user.

As can be seen readily in FIG. 1, the piezoelectric crystal 28 resonates, expands and contracts volumetrically, converting electronic energy into sound-wave energy. This energy is coupled to the bristles, and also to the entire volume of the brush-head 32. When the brush is used on a daily basis to clean teeth, the ultrasonic vibrations are also transferred to the tissues inside the oral cavity, in particular to the lips and facial tissues of the user through the back side of the brush head 32 as it rubs against the inside surfaces of the oral cavity. These ultrasonic vibrations have been shown to have therapeutic effects on recurrent aphthous stomatitis, commonly known as canker sores by reducing recurrence of the ulcers both in frequency and severity. Thus, the invention achieved therapeutic action in the oral cavity when employed as a cleansing device.

Figure 8:
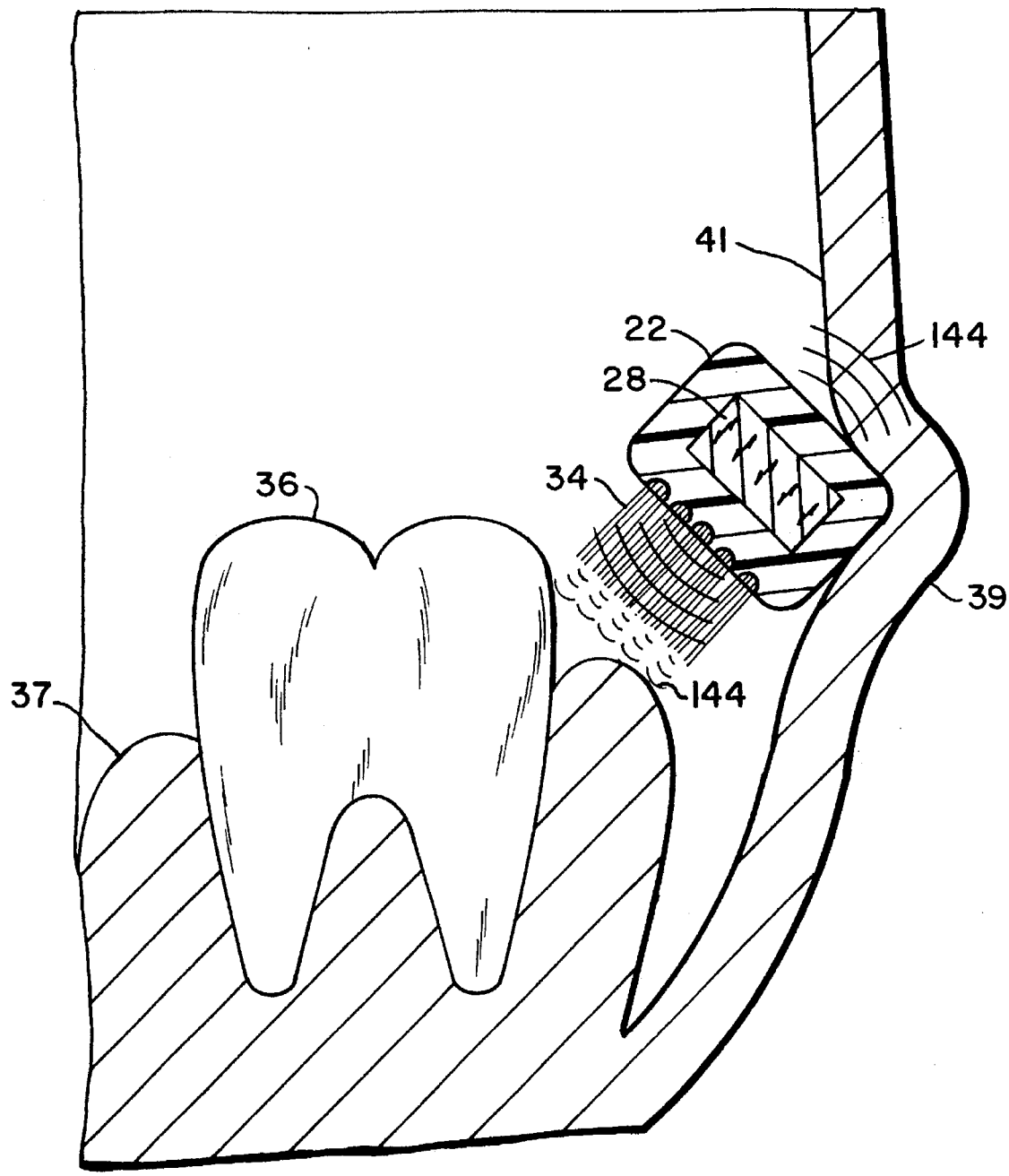
FIG. 8 illustrates schematically a device according to the invention for delivering directionally ultrasonic energy to the teeth, gums, and facial tissues.

FIG. 8 illustrates another embodiment of a therapeutic ultrasonic toothbrush according to the invention. A piezoelectric transducer 28, located within the handle 22, expands and contracts in tune with the ultrasonic frequency electrical pulses applied by an ultrasonic power supply (not shown). Generated ultrasonic waves 144 are coupled to the teeth 36 and gums 37 by the bristle clusters 34 and to the inner surfaces 41 of the facial tissues 39 by the handle 22.

Figure 9A:
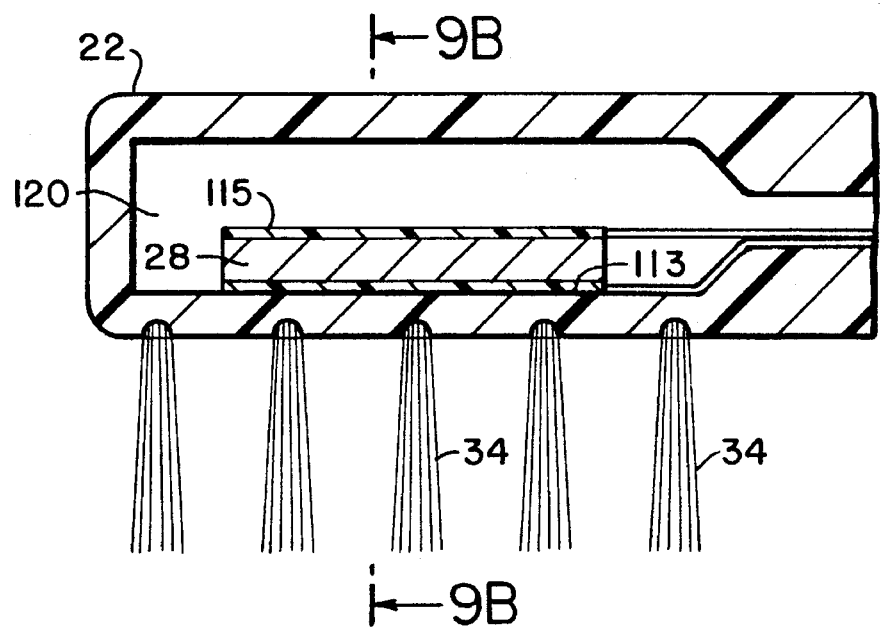
FIG. 9A illustrates in a schematic cross section an embodiment of a device for delivering ultrasonic energy toward the bristle side of the device.
Figure 9B:
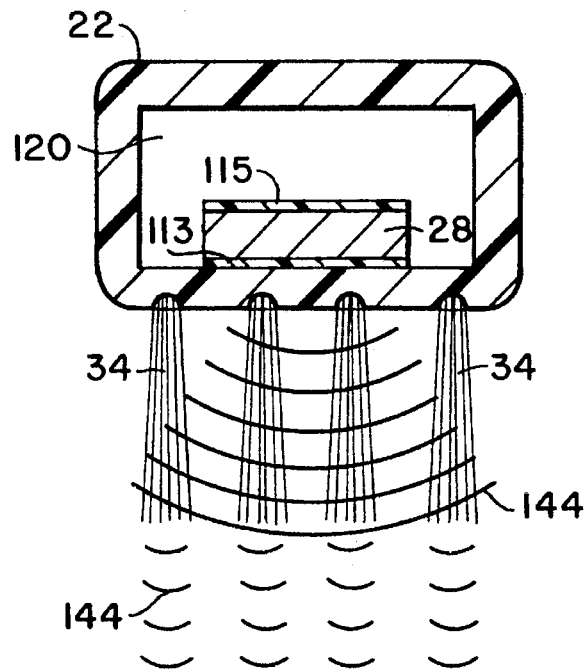
FIG. 9B is a cross section taken along line 9B—9B of FIG. 9A.

FIGS. 9A and 9B show an embodiment where it is desired to increase energy output from the side 113 of the transducer 28 which is attached to the handle 22 holding the bristles 34. According to the invention, the way to provide increased output from side 113 of the transducer 28 is to isolate the opposing side 115 from the surrounding materials by an air gap 120 formed within the handle 22. The air gap may be filled with a foam like material, if desired. Due to the mismatch of acoustic impedance between the air gap 120 and the transducer 28, little or substantially no ultrasonic energy will be radiated from the side 115 of the transducer 28. The ultrasonic energy is then effectively captured within the transducer 28 and radiated out on the side 113 of the transducer 28 that is rigidly attached to the handle 22. The ultrasonic energy is radiated through the handle 22 and the bristles 34 in form of ultrasonic waves 144. Alternatively, an acoustic damper (not shown) may be located in the air gap as an absorber.

Bacterial contamination of the oral cavity is a common health problem that manifests itself not only in gingivitis and periodontitis affecting the gums, but also in recurring aphthous stomatitis (canker sores) affecting the inner surfaces of the lips and other facial tissues. Significant improvement of the therapeutic ultrasonic toothbrush according to the invention can be achieved by radiating ultrasonic waves 144 from the complete circumference of the toothbrush head. Ultrasonic waves 144 transmitting to the mucus membranes of the inside of the mouth weaken the bacteria causing apthhous stomatitis and speed up healing of the sores in addition to the impact on the bacteria within the gums causing gingivitis and periodontitis of the gums.

Figure 10A:
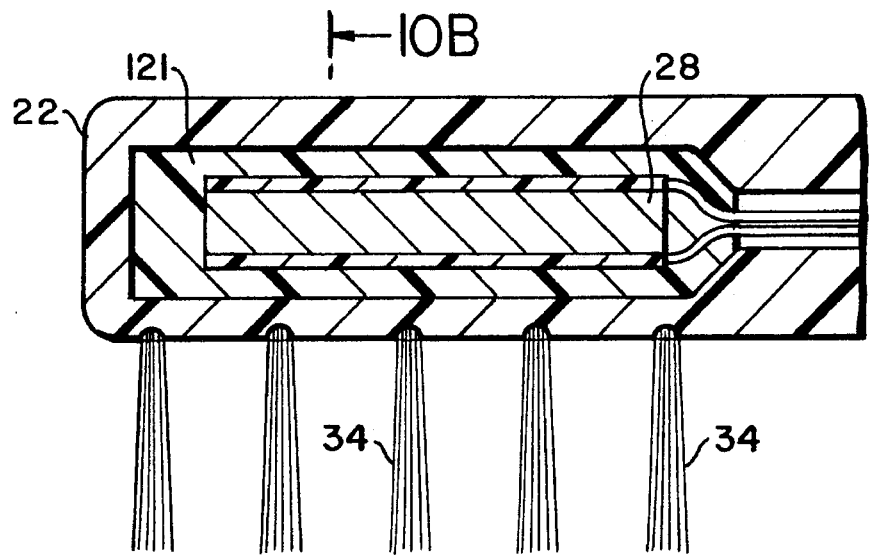
FIG. 10A illustrates in a schematic cross section an embodiment of a device for delivering ultrasonic energy with circumferential radiation.
Figure 10B:
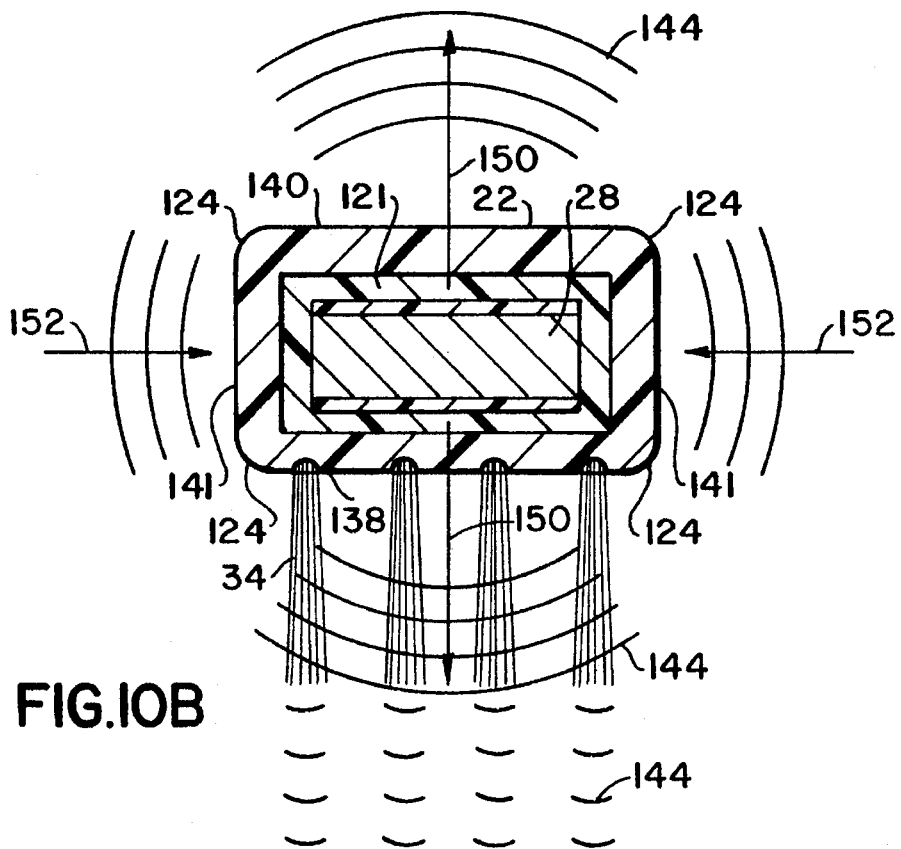
FIG. 10B is a cross section taken along line 10B—10B of FIG. 10A.

FIGS. 10A and 10B, illustrate an embodiment of the invention, to harness the maximum amount of the available energy from the transducer 28, and to radiate it circumferentially. According to the invention, the transducer 28 is encapsulated within a flexible material 121 having acoustic impedance that matches the quarter wavelength of the transducer 28. The material 121 fills the handle 22 around the transducer 28. The handle 22 carries the bristles 34 on side 138 to transmit ultrasonic waves 144 to the gums and transmits ultrasonic waves 144 to the inside of the lips and facial tissues through the entire circumference of the handle 22 and particularly strongly through respective rim and internal sides 140 and 141.

As the transducer 28 expands in the direction with arrows 150 it forces the handle 22 to expand in the same direction. The sides of the handle 22 at 90 degrees from the expanding sides will contract in the direction with arrows 152, to maintain a relatively constant volume of the device. When the transducer 28 contracts, the motions of the handle 22 change direction. The expanding and contracting sides of handle 22 will resonate in tune with the transducer 28 in a substantially complete circumferential mode. Limited dead spots 124 may occur at the crossover point of the expanding and contracting segments of the handle 22. Encapsulation of the transducer 28, according to the invention, provides for the multidirectional transmission of the ultrasonic waves 144 both through the bristles 34 and the handle 22 at the high efficiency.

Figure 11A:
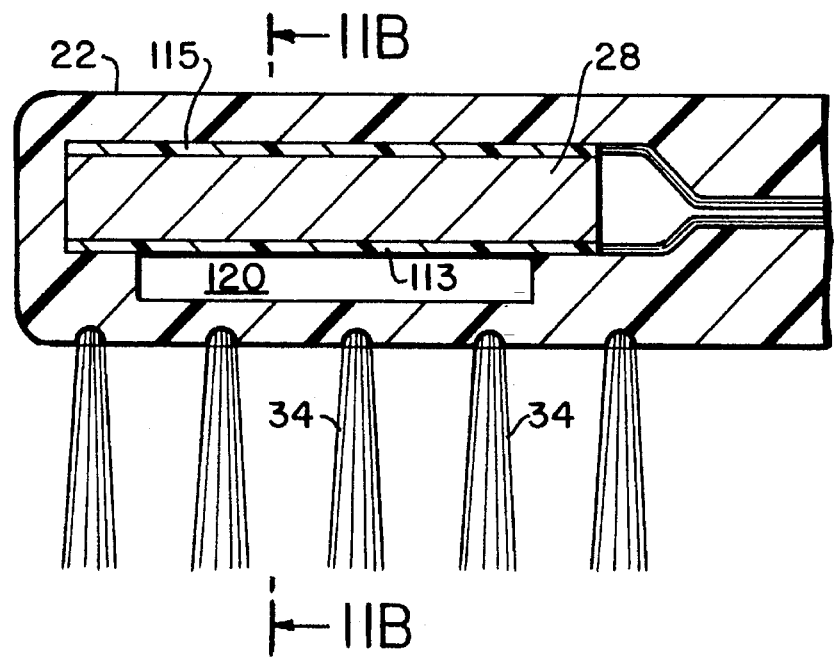
FIG. 11A illustrates in a schematic cross section a device for delivering ultrasonic energy away from the bristle side toward the back and lateral sides of the device.
Figure 11B:
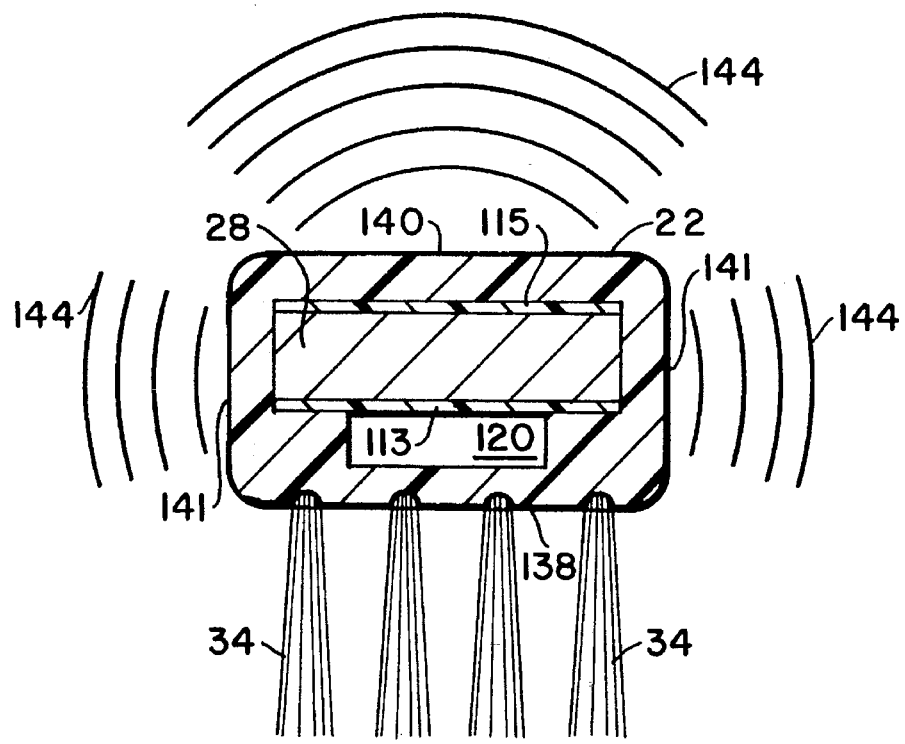
FIG. 11B is a cross section taken along line 11B—11B of FIG. 11A.
Figure 12:
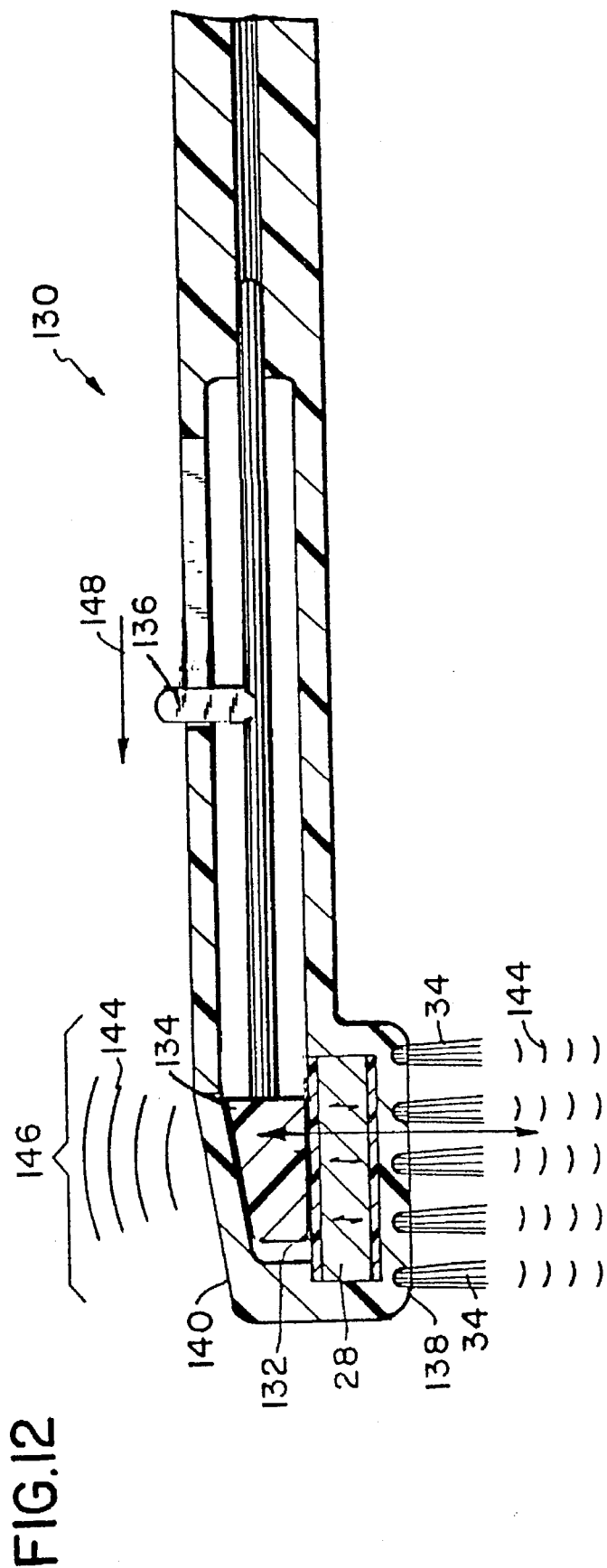
FIG. 12 illustrates in a schematic cross section a switchable device where the user has the capability to direct the ultrasonic output toward the bristle side or to switch to a mode, as shown, where the ultrasonic energy is emitted toward the back and sides of the handle in addition to the bristle side.
Figure 12C:
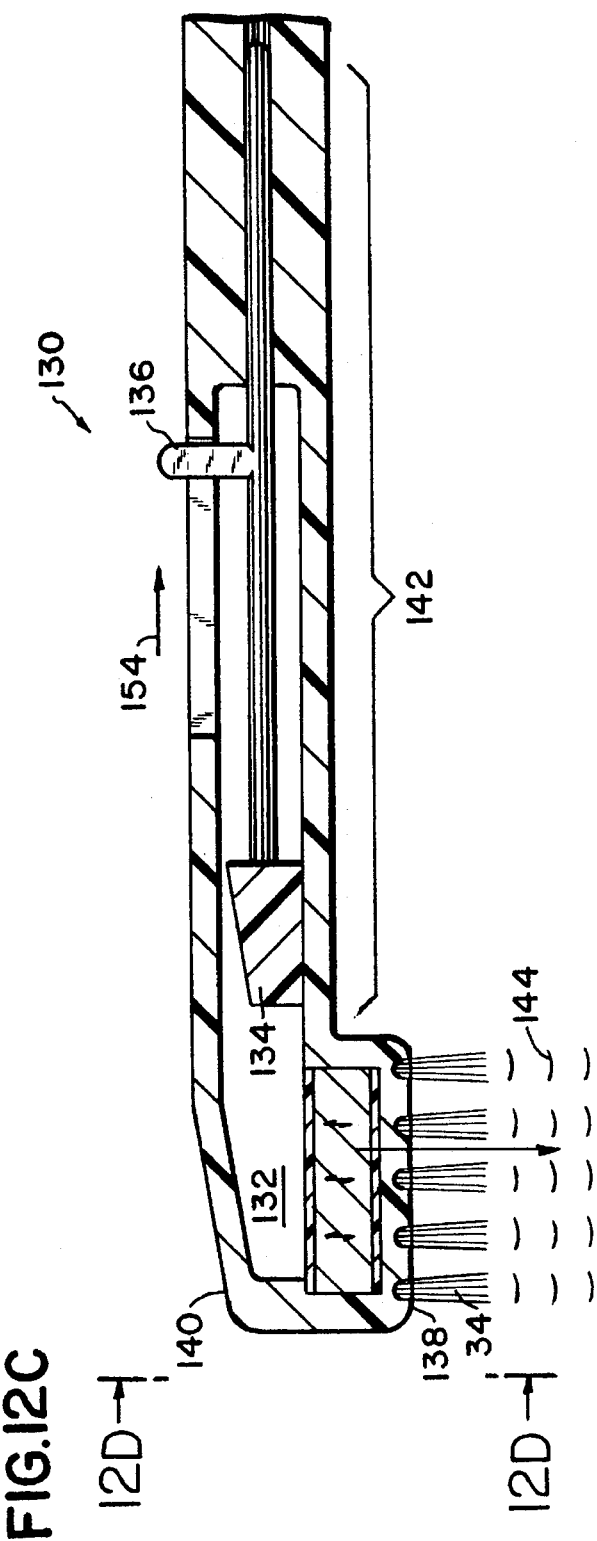
FIG. 12C is a side section similar to FIG. 12 where the device is switched to deliver ultrasonic energy toward the bristle side.
Figure 12D:
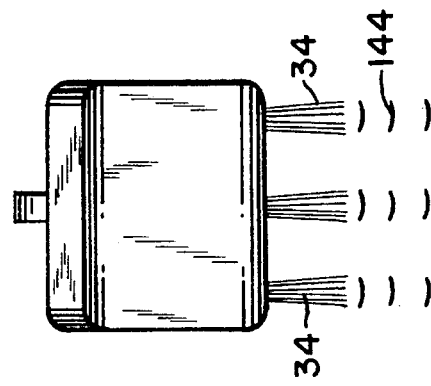
FIG. 12D is an end view of FIG. 12C.

For applications where severe recurring aphthous stomatitis (canker sores) affecting the inner surfaces of the lips and other facial tissues outweigh the importance to fight gingivitis of the gums, it may be desirable to re-direct the majority of the ultrasonic waves 144 toward the mucus membranes and direct less toward the teeth and gums of the user. FIGS. 11A and 11B illustrate an embodiment of the invention which is adapted to achieve such a result. Side 115 of transducer 28 is directly coupled to the sides 140 and 141 of handle 22 opposite to side 138 carrying bristles 34. An air gap 120 is provided on side 113 of the transducer 28 adjacent to bristles to block radiation of ultrasonic waves toward side 138 of handle 22 and the bristles 34.

FIGS. 12 and 12A–12D illustrate an alternative construction 130 of the therapeutic ultrasonic toothbrush according to the invention. A switchable configuration of a device 130 is provided where the user has the option to focus the ultrasonic energy to the bristles 34 embedded in side 138 of the toothbrush head 146 to achieve ultimate treatment for gingivitis, or to distribute the energy circumferentially around the toothbrush head 146 both to the bristles 34 embedded in side 138 and to the other sides 140 and 141 to treat recurrent aphthous stomatitis in addition to performing daily oral hygiene care.

The device 130 includes a piezoelectric transducer 28 mounted internally onto the side 138 of the toothbrush head 146 opposite the brushes 34. The transducer 28 is backed by a tapered air gap 132 preventing radiation of ultrasonic energy to all directions other than toward side 138 and the bristles 34. A movable tapered wedge 134 matching the configuration of the air gap 132, is formed of an appropriate material having acoustic impedance characteristics that matches or enhances the transmission of the piezoelectric transducer 28, e.g., maximum transmission at the quarter wavelength. A slider mechanism 136 is attached to the wedge 134 and allows the user to move the wedge 134 into the air gap 132, in direction with arrow 148 (FIG. 12A) filling the air gap 132 forcefully by virtue of the tapered design to transmit a portion of ultrasonic waves 144 to the back 141 of the toothbrush head 146. Withdrawal of the wedge 134 from the air gap 132 in direction of arrow 154 (FIG. 12C) into the hollow handle 142 reestablishes the air gap 132, and isolates the side of the transducer. An opposite configuration may also be desirable at times when ultrasonic output is desired toward the mucus membranes. In such an arrangement (not shown), the tapered air gap 132 would be placed on the side of the bristles 34 of the brush head 146 and the transducer 28 would be attached to the sides 140 and 141 of the brush head 146. Emission of the ultrasonic energy would then be directed toward sides 140 and 141 when the wedge 134 is not filling the air gap 132. When the wedge is forced into the air gap 132, total circumferential radiation is reestablished. In yet another embodiment, the wedge 134 may be a damper such as foamed or unfoamed elastomeric.

In an exemplary embodiment the piezoelectric transducer is a lead zirconate titanate (PZT) ceramic. The wedge may be a PZT ceramic or a polyphenelene oxide (PPO) or other appropriate material having a desirable transmission characteristic, e.g., maximum transmission at the quarter wavelength of the power supply frequency. The frequency may be varied for the desired result. A useful frequency is 1.6 MHz. The operating frequency may also be amplitude modulated, frequency modulated, pulse-width modulated and with or without a variable duty cycle.

The handle may be likewise formed of a PPO material. The transducer may be secured in the handle by a variety of materials, including a hot melt adhesive such as ethylene vinyl acetate (EVA) or an epoxy resin with an appropriate transmission characteristic. The transmission characteristic may be determined empirically.

In yet another embodiment of the invention, the electrical signals driving the transducer may be varied to produce variable amplitude and frequency signals or combinations thereof. Also, the signals may be pulse width and frequency modulated to cause vibrations in one or more of the sonic, subsonic and ultrasonic ranges. For example, a sonic or subsonic pulse width modulated (PWM) signal may be employed as an envelope for a high frequency signal. Also, the power and duty cycle of such signals may be varied as desired.

It can be seen that the invention provides a safe and effective ultrasonic toothbrush that can be utilized by any novice in the daily maintenance of oral hygiene. The fluid coupled ultrasonic energy, where metallic contact with the teeth has been eliminated, and the relatively low level but effective energy provides outstanding safety for both the teeth and the surrounding soft tissue. The reduced energy requirement is made possible by the controlled distance between the piezoelectric transducer and the teeth, that is established by the length of the bristle clusters. In particular, the removable toothbrush head allows for frequency replacement of the bristle clusters as appropriate. Finally, daily use of the device results in an effective treatment for mouth sores and a reduction in the severity and frequency of such mouth sores when they occur.

While the preceding description contains many specificities, these should not be construed as limitations on the scope of the invention, but rather as an exemplification of a preferred and additional embodiments thereof. Many other variations are possible. Skilled artisans will readily be able to change dimensions, shapes and construction materials of the various components described in the embodiments and adapt the invention to various sonic energy applications, from the subsonic range through the ultrasonic range. Thus, in the appended claims the vibrations and electric signals should be considered to include such range of frequencies. Accordingly, the scope of the invention should be determined not by the embodiments illustrated, but by the appended claims and their legal equivalents.

What is claimed:

1. A therapeutic oral hygiene device to remove soft plaque from teeth and gums and to treat gingivitis of the gums and recurring aphthous stomatitis of the oral cavity, comprising:
   a rigid elongated member having a handle end and a bristle end;
   a piezoelectric transducer secured to the elongated member adjacent the bristle end for contracting and expanding volumetrically in response to a changing electrical field, said transducer having first and second active surface portions for generating and radiating vibrations operative to at least one of (a) to loosen plaque on the surface of the teeth and disrupt the bacterial colonization process in the gingival pockets; and (b) to reduce recurrence of aphthous stomatitis and accelerate healing of the sores of the mucous membranes of the oral cavity without appreciable relative movement of the bristle end with respect to the handle end;
   means coupled to the piezoelectric transducer operative for generating electric signals and transmitting said signals to said piezoelectric transducer;
   a plurality of bristle clusters secured to a side of the handle of the elongated member adjacent the first active surface portion of the piezoelectric transducer, said bristle clusters to be received within the mouth for conducting said vibrations to the tooth and gums to be and moved across tooth and gingival surfaces for dislodging the plaque therefrom;
   a side of the handle adjacent the second active surface portion of the transducer to contact the inside surfaces of the oral cavity for acoustically coupling the energy to the said inside surfaces of the oral cavity while the brush is moved across tooth and gingival Surfaces to reduce recurrence of aphthous stomatitis and to accelerate healing of the sores of the mucous membranes of the oral cavity.

2. The therapeutic oral hygiene device according to claim 1 further including means for selecting the first and second active surface portions to selectively radiate ultrasonic energy.

3. The device of claim 1 wherein the electrical signals and vibrations are at least one of a subsonic, sonic and ultrasonic frequency.

4. The device of claim 1 further comprising a removable brush holder for the bristles.

5. The device of claim 1 wherein the bristle clusters extend laterally from the elongated member opposite the piezoelectric transducer to space said transducer from the teeth.

6. The device of claim 1 wherein said handle is formed with an opening for receiving the transducer therein, and includes means for acoustically isolating one of the first or second active surface portions of said transducer from the bristles and the handle.

7. The device of claim 6 including selective acoustic coupling means secured between the transducer and the handle operative between two positions for selectively coupling and decoupling said first active surface portion of said transducer with said handle.

8. The device of claim 6 including selective acoustic coupling means secured between the transducer and the handle operable between two positions for selectively coupling and decoupling the second active surface portion of said transducer with said handle.

9. The device of claim 1 further comprising means for encapsulating the piezoelectric transducer and providing enhanced multidirectional and substantially circumferential energy radiation from the handle.

10. The device of claim 1 further comprising:
    isolating means to acoustically isolate one of the first and second active surface portions of the transducer from the handle for reducing transmission of energy through one of the bristles and the handle.

11. The device of claim 10 wherein the isolating means comprises an air gap between one of the first and second surface positions of the handle.

12. The device of claim 1 further comprising encapsulating means on at least one of the first and second surface portions for providing enhanced energy radiation toward the handle.

13. The device of claim 1 wherein the electrical signals are in the form of at least one of an amplitude modulated and frequency modulated signal.

14. The device of claim 1 wherein the electrical signals are in the form of at least one of a pulse width modulated signal and a variable duty cycle signal.

15. The device of claim 1 further including means for immobilizing at least one of the active surfaces.

16. The therapeutic oral hygiene device according to claim 15 further including means for selecting the first and second active surface portions to selectively radiate ultrasonic energy.

17. The device of claim 15 further comprising a removable brush holder secured to the bristle support.

18. The device of claim 1 wherein the electrical signals are in the form of at least one of a pulse width modulated signal and a variable duty cycle signal.

19. A therapeutic oral hygiene device to remove soft plaque from teeth and gums and to treat gingivitis of the gums and recurring aphthous stomatitis of the oral cavity, comprising:
    an elongated substantially rigid handle member having opposite ends in spaced apart relation;
    a removable bristle support secured to the handle near one end thereof;
    a piezoelectric transducer secured within the bristle support and responsive when energized for contracting and expanding volumetrically in response to a changing electrical field, said transducer having at least two active surface portions for generating and radiating vibrations and operative to at least one of (a) to loosen plaque on the surface of the teeth and disrupt the bacterial colonization process in the gingival pockets; and (b) to reduce recurrence of aphthous stomatitis and accelerate healing of the sores of the mucous membranes of the oral cavity;

means coupled to the piezoelectric transducer operative for generating electric signals and transmitting said signals for energizing said piezoelectric transducer;

a plurality of bristle clusters for engaging the teeth surfaces and the gums and being secured to at least one side of the bristle support adjacent the piezoelectric transducer and extending transversely of the support for conducting the vibrations to the teeth and gums and moving across tooth and gingival surfaces and without appreciable relative movement between the bristle clusters and the handle and dislodging the plaque from the teeth;

means on a side of the bristle support remote from the bristles to contact the inside surfaces of the oral cavity for acoustically coupling the energy to the said inside surfaces of the oral cavity while the brush is moved across tooth and gingival surfaces to reduce recurrence of aphthous stomatitis and to accelerate healing of the sores of the mucous membranes of the oral cavity.

20. The device of claim 19 wherein the electrical signals and vibrations are at least one of a sonic, subsonic and ultrasonic frequency.

21. The device of claim 19 further comprising encapsulating means for encapsulating the transducer within the bristle support for providing multidirectional and substantially circumferential energy radiation.

22. The device of claim 19 further comprising:

means for acoustically isolating one of the two active surface portions of the transducer from the bristle support for reducing transmission of energy through the isolated side of the transducer.

23. The device of claim 19 further comprising partial transducer encapsulating means for encapsulating at least one side of the transducer providing enhanced radiation of energy from the encapsulated side.

24. The device of claim 19 wherein the electrical signals are in the form of at least one of an amplitude modulated and frequency modulated signal.

25. A therapeutic dental hygiene device comprising:

a rigid elongated member of non-conductive material having a handle end and a bristle end;

a piezoelectric transducer secured to the elongated member adjacent the bristle end for contracting and expanding volumetrically in response to a changing electrical field generating vibrations;

means coupled to the piezoelectric transducer operative for generating electrical signals and transmitting said signals to said piezoelectric transducer;

a plurality of bristle clusters for carrying dentifrice;

means supporting the bristle clusters on the bristle end of the elongated member secured to the elongated member adjacent the piezoelectric transducer, said bristle clusters to be received within the human mouth and moved across tooth and gingival surfaces for dislodging the loosened soft plaque therefrom, and said means for supporting the bristle clusters having external surfaces adjacent said bristle clusters for contacting mouth tissue inside the oral cavity for reducing the recurrence and severity of mouth sores.

26. The device of claim 25 further comprising means for securing the piezoelectric transducer to the handle.

27. The device of claim 25 wherein the electrical signals and vibrations are at least one of a subsonic, sonic and ultrasonic frequency.

28. The device of claim 25 wherein the electrical signals are in the form of at least one of an amplitude modulated and frequency modulated signal.

29. The device of claim 25 wherein the electrical signals are in the form of at least one of a pulse width modulated signal and a variable duty cycle signal.

30. The device of claim 25 wherein the handle and the means for securing the transducer to the handle carry energy at a quarter wavelength of the frequency of the energy signals.

* * * * *